United States Patent [19]

Wenderoth et al.

[11] Patent Number: 5,116,866
[45] Date of Patent: May 26, 1992

[54] ANILINE DERIVATIVES AND FUNGICIDES CONTAINING THEM

[75] Inventors: Bernd Wenderoth, Lampertheim; Franz Schuetz, Ludwigshafen; Hubert Sauter, Mannheim; Franz Roehl; Eberhard Ammermann, both of Ludwigshafen; Gisela Lorenz, Neustadt, all of Fed. Rep. of Germany

[73] Assignee: BASF Aktiengesellschaft, Ludwigshafen, Fed. Rep. of Germany

[21] Appl. No.: 588,837

[22] Filed: Sep. 27, 1990

[30] Foreign Application Priority Data

Sep. 29, 1989 [DE] Fed. Rep. of Germany ....... 3932542

[51] Int. Cl.⁵ .............................................. A01N 37/34
[52] U.S. Cl. ...................................... 514/522; 514/539; 558/414; 560/21; 560/35
[58] Field of Search ............... 560/21, 35; 558/414; 514/522, 539

[56] References Cited

U.S. PATENT DOCUMENTS

| | | | |
|---|---|---|---|
| 4,829,085 | 5/1989 | Wenderoth et al. | 574/522 |
| 4,999,042 | 3/1991 | Anthony et al. | 560/35 |

FOREIGN PATENT DOCUMENTS

| | | |
|---|---|---|
| 254426 | 1/1988 | European Pat. Off. |
| 278595 | 8/1988 | European Pat. Off. |
| 335519 | 10/1989 | European Pat. Off. |
| 2192883 | 1/1988 | United Kingdom ........ 560/35 |

Primary Examiner—Bruce Gray
Attorney, Agent, or Firm—Oblon, Spivak, McClelland, Maier & Neustadt

[57] ABSTRACT

Aniline derivatives of the formula

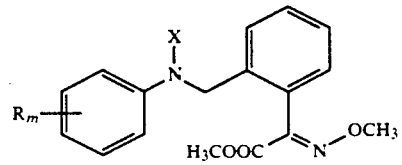

where
R is hydrogen, halogen, cyano, nitro, alkyl, cycloalkyl, alkenyl, alkoxy, haloalkyl, haloalkoxy, or substituted or unsubstituted phenyl, phenoxy, benzyl or benzyloxy,
m is an integer from 1 to 5 or the group

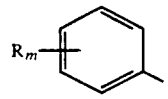

α-naphthyl or β-naphthyl and
X is hydrogen, alkyl or cycloalkyl,
their plant-tolerated acid addition salts and metal complexes, and their use for combating fungi.

6 Claims, No Drawings

ANILINE DERIVATIVES AND FUNGICIDES CONTAINING THEM

The present invention relates to novel aniline derivatives of the general formula I

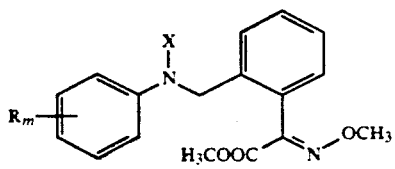

(I)

where
R is hydrogen, halogen, cyano, nitro, $C_1$-$C_{15}$-alkyl, $C_3$-$C_6$-cycloalkyl, $C_3$-$C_6$-alkenyl, $C_1$-$C_4$-alkoxy, $C_1$- or $C_2$-haloalkyl, $C_1$- or $C_2$-haloalkoxy, unsubstituted or substituted phenyl, unsubstituted or substituted phenoxy, unsubstituted or substituted benzyl or unsubstituted or substituted benzyloxy,
m is an integer of from 1 to 5 or the group

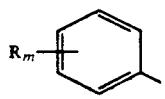

α-naphthyl or β-naphthyl and
X is hydrogen, $C_1$-$C_6$-alkyl or $C_3$-$C_6$-cycloalkyl, and their plant-tolerated acid addition salts and metal complexes.

It is known that oxime ether derivatives, for example 2-phenoxymethylphenylglyoxylic acid methyl ester O-methyl oxime, can be used as fungicides (EP-A-253213). However, their action is insufficient for some indications.

It is an object of the present invention to provide novel fungicidal active ingredients having an oxime ether structure.

We have found that this object is achieved by the aniline derivatives I defined at the outset. The present invention furthermore relates to a process for the preparation of the aniline derivatives I and to fungicides which contain the aniline derivatives I as active ingredients.

The radicals stated in the general formula I may have, for example, the following meanings: R may be identical or different and may be hydrogen, halogen, e.g. fluorine, chlorine, bromine or iodine, cyano, nitro, $C_1$-$C_{15}$-alkyl, preferably $C_1$-$C_8$-alkyl, in particular $C_1$-$C_4$-alkyl, e.g. methyl, ethyl, n-propyl, isopropyl, n-butyl, isobutyl, sec-butyl, tert-butyl, pentyl, hexyl, n-heptyl, 1,1,3-trimethylbutyl, n-octyl, 1,1,3,3-tetramethylbutyl, nonyl, decyl, dodecyl, tridecyl or tetradecyl, $C_3$-$C_6$-cycloalkyl, e.g. cyclopropyl, cyclopentyl or cyclohexyl, $C_3$-$C_6$-alkenyl, e.g. 1-propenyl or 2-propenyl, $C_1$-$C_4$-alkoxy, e.g. methoxy, ethoxy, n-propoxy, isopropoxy, n-butoxy or tert-butoxy, $C_1$- or $C_2$-haloalkyl, e.g. difluoromethyl, trifluoromethyl, trichloromethyl, dichloromethyl, trichloromethyl or pentafluoroethyl, $C_1$- or $C_2$-haloalkoxy, e.g. trifluoromethoxy, difluoromethoxy, tetrafluoroethoxy or pentafluoroethoxy, unsubstituted or substituted phenyl, e.g. phenyl, $C_1$-$C_4$-alkylphenyl, such as 2-isopropylphenyl or 2-methylphenyl, halophenyl, such as 2-chlorophenyl, unsubstituted or substituted phenoxy, e.g phenoxy, $C_1$-$C_4$-alkylphenoxy, such as 2-methylphenoxy, halophenoxy, such as 2-chlorophenoxy, unsubstituted or substituted benzyl, e.g. benzyl, halobenzyl, such as 2-chlorobenzyl, unsubstituted or substituted benzyloxy, e.g. benzyloxy, halobenzyloxy or $C_1$-$C_4$-alkylbenzyloxy, such as 2-chlorobenzyloxy, 2-methylbenzyloxy or 4-tert-butylbenzyloxy. The alkyl, alkenyl, alkoxy and haloalkyl radicals may be straight-chain or branched. The same applies to the corresponding substituents of the phenyl, phenoxy, benzyl and benzyloxy radicals. The number of substituents of the last-mentioned radicals may be from 1 to 3.

Preferred radicals R are hydrogen, halogen, in particular fluorine, and $C_1$-$C_4$-alkyl, in particular methyl.

m is 1, 2, 3, 4 or 5, preferably 1, 2 or 3.

X is hydrogen, straight-chain or branched $C_1$-$C_6$-alkyl, preferably $C_1$-$C_4$-alkyl, e.g. methyl, ethyl, n-propyl, isopropyl, n-butyl, isobutyl, sec-butyl, tert-butyl, pentyl or hexyl, or $C_3$-$C_6$-cycloalkyl, e.g. cyclopropyl, cyclopentyl, cyclohexyl. X is in particular methyl.

The novel aniline derivatives I can also be converted by reaction with acids into plant-tolerated acid addition salts of the inorganic or organic acids, for example into salts of hydrochloric acid, hydrobromic acid, nitric acid, oxalic acid, acetic acid, sulfuric acid, phosphoric acid or dodecylbenzenesulfonic acid. The activity of the salts is due to the cation, so that the anion generally has no effect.

The compounds I may furthermore be converted into metal complexes by known methods. This can be achieved by reacting these compounds with metal salts, for example salts of the metals copper, zinc, iron, manganese or nickel, e.g. copper(II) chloride, zinc(II) chloride, iron(III) chloride, copper(II) nitrate, manganese(II) chloride or nickel(II) bromide.

Because of the C=N double bonds, the compounds I may occur both as E isomers and as Z isomers. Both the individual isomeric compounds and mixtures thereof form subjects of the invention and can be used as fungicidal active ingredients.

The compounds I can be prepared, for example, by the following process:

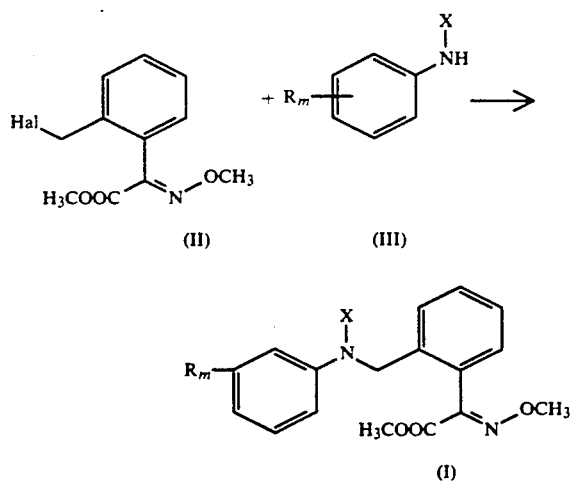

A benzyl halide of the general formula II, where Hal is chlorine, bromine or iodine, is reacted with an aniline of the general formula III, where R, m and X have the abovementioned meanings, in a suitable organic solvent, for example toluene or N,N-dimethylformamide, in the presence or absence of a suitable catalyst, such as potassium iodide or sodium iodide, by a conventional method (J. March, Advanced Organic Chemistry, 3rd edition, 1985 pages 364-366, J. Wiley & Sons, New York) at from 20° to 120° C., preferably from 100° to 120° C.

The substituted benzyl halides of the general formula II where Hal is chloride or bromide are obtained by halogenating the 2-methylphenylglyoxylic acid methyl ester O-methyl oxime IV by methods known from the literature. This is achieved, for example, using bromine or chlorine in an inert solvent (e.g. tetrachloromethane), with or without exposure to a light source (for example a 300 W Hg vapor lamp) or by reaction with N-chloro- or N-bromosuccinimide (Horner and Winkelmann, Angew. Chem. 71, (1959), 349).

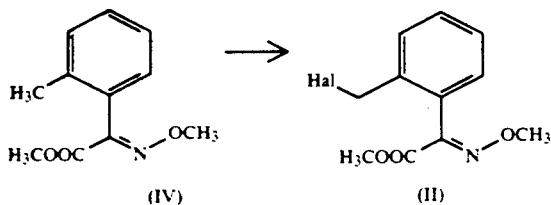

Compound II in which Hal is iodide can be prepared by reaction with sodium iodide in acetone (Miller and Nunn, J. Chem. Soc., Perkin Trans I, (1976), 416). 2-Methylphenylglyoxylic acid methyl ester O-methyl oxime IV can be obtained by reacting methyl 2-methylphenylglyoxylate V with, for example, a) O-methylhydroxylamine hydrochloride or b) hydroxylamine hydrochloride to give the corresponding oxime and methylating this oxime with a conventional methylating agent of the formula CH$_3$—L in which L is a leaving group, e.g. chloride, bromide, iodide or methylsulfate (cf. DE-A-36 23 921).

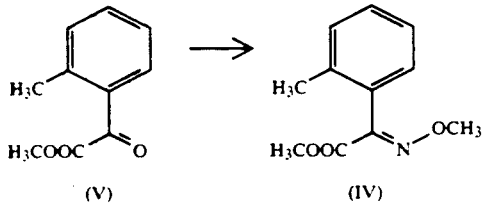

Benzyl halides of the general formula II, where Hal is chloride, bromide or iodide, are furthermore obtained if a methyl 2-halomethylphenyloxylate VI is a) reacted with O-methylhydroxylamine hydrochloride or b) reacted with hydroxylamine hydrochloride to give the corresponding oxime and the latter is reacted with a methylating agent of the formula CH$_3$—L, where L is a leaving group, e.g. chloride, bromide, iodide or methylsulfate (DE-A-36 23 921).

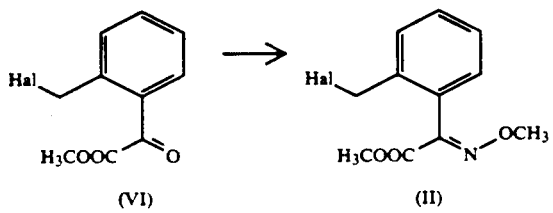

Methyl 2-halomethylphenylglyoxylates of the formula VI where Hal is chloride or bromide can be prepared by halogenating methyl 2-methylphenylglyoxylate V by methods known from the literature. The reaction is carried out, for example, using bromine or chlorine in an inert solvent (e.g. tetrachloromethane), with or without exposure to a light source (for example a 300 W Hg vapor lamp), or using N-chloro- or N-bromosuccinimide (Horner and Winkelmann, Angew. Chem. 71 (1959), 349).

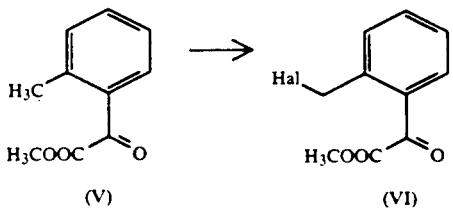

Compound VI in which Hal is iodide can be prepared from the chloride or bromide by reaction with sodium iodide in acetone by a method known from the literature (J. Chem. Soc., Perkin Trans. I, (1976), 416).

PREPARATION EXAMPLES

EXAMPLE 1 a) 21.4 g (0.133 mol) of bromine are added, while stirring, to 27.6 g (0.133 mol) of 2-methylphenylglyoxylic acid methyl ester O-methyl oxime dissolved in 400 ml of tetrachloromethane. Refluxing is then carried out for four hours with exposure to a 300 W Hg vapor lamp. Thereafter, the mixture is evaporated down, the residue is taken up in ethyl acetate/water and the solution is washed with water, dried with sodium sulfate and evaporated down. The crude product is purified by chromatography over silica gel using 9:1 cyclohexane/ethyl acetate. 17.4 g (46% of theory) of 2-bromomethylphenylglyoxylic acid methyl ester O-methyl oxime are obtained as an oil.

b) 6.4 g (60 mmol) of N-methylaniline, 8.6 g (30 mmol) of 2-bromomethylphenylglyoxylic acid methyl ester O-methyl oxime and about 100 mg of potassium iodide in 100 ml of toluene are refluxed for 7 hours while stirring. The mixture is cooled, washed several times with water, dried over sodium sulfate and then evaporated down. 9 g (96% of theory) of 2-[(N-methyl-N-phenyl)aminomethyl]-phenylglyoxylic acid methyl ester O-methyl oxime (Table 1, No. 1) are obtained (mp.=90°-92° C.). $^1$H-NMR: δ=2.95 (s, 3H); 3.75 (s, 3H); 4.05 (s, 3H); 4.35 (s, 2H); 6.65-7.35 (m, 9H).

The active ingredients shown in Table 1 can be prepared similarly to processes described by J. March, Advanced Organic Chemistry, 3rd edition, 1985, pages 364-366 and in Example 1.

TABLE 1

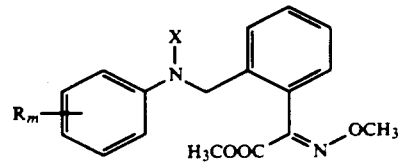

(I)

| No. | $R_m$ | X | mp (°C.)/ IR (cm$^{-1}$) |
|---|---|---|---|
| 1 | H | CH$_3$ | 90-92/ |

TABLE 1-continued

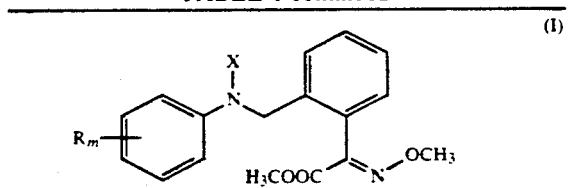

(I)

| No. | $R_m$ | X | mp (°C.)/ IR (cm$^{-1}$) |
|---|---|---|---|
| | | | 2935,1725, 1600,1507, 1215,1069, 1017,751 |
| 2 | 2-F | CH$_3$ | |
| 3 | 3-F | CH$_3$ | 101–102/ 2935,1723, 1620,1502, 1214,1066, 1014,761 |
| 4 | 4-F | CH$_3$ | 73–75/ 2940,1725, 1512,1227, 1069,1017, 819 |
| 5 | 2,3-F$_2$ | CH$_3$ | |
| 6 | 2,4-F$_2$ | CH$_3$ | |
| 7 | 2,4,6-F$_3$ | CH$_3$ | |
| 8 | 2,3,4,5,6-F$_5$ | CH$_3$ | |
| 9 | 2-Cl | CH$_3$ | |
| 10 | 3-Cl | CH$_3$ | |
| 11 | 4-Cl | CH$_3$ | |
| 12 | 2,3-Cl$_2$ | CH$_3$ | |
| 13 | 2,4-Cl$_2$ | CH$_3$ | |
| 14 | 2,5-Cl$_2$ | CH$_3$ | |
| 15 | 2,6-Cl$_2$ | CH$_3$ | |
| 16 | 3,4-Cl$_2$ | CH$_3$ | |
| 17 | 3,5-Cl$_2$ | CH$_3$ | |
| 18 | 2,3,4-Cl$_3$ | CH$_3$ | |
| 19 | 2,3,5-Cl$_3$ | CH$_3$ | |
| 20 | 2,3,6-Cl$_3$ | CH$_3$ | |
| 21 | 2,4,5-Cl$_3$ | CH$_3$ | |
| 22 | 2,4,6-Cl$_3$ | CH$_3$ | |
| 23 | 3,4,5-Cl$_3$ | CH$_3$ | |
| 24 | 2,3,4,6-Cl$_4$ | CH$_3$ | |
| 25 | 2,3,5,6-Cl$_4$ | CH$_3$ | |
| 26 | 2,3,4,5,6-Cl$_5$ | CH$_3$ | |
| 27 | 2-Br | CH$_3$ | |
| 28 | 3-Br | CH$_3$ | |
| 29 | 4-Br | CH$_3$ | |
| 30 | 2,4-Br$_2$ | CH$_3$ | |
| 31 | 2,5-Br$_2$ | CH$_3$ | |
| 32 | 2,6-Br$_2$ | CH$_3$ | |
| 33 | 2,4,6-Br$_3$ | CH$_3$ | |
| 34 | 2,3,4,5,6-Br$_5$ | CH$_3$ | |
| 35 | 2-I | CH$_3$ | |
| 36 | 3-I | CH$_3$ | |
| 37 | 4-I | CH$_3$ | |
| 38 | 2,4-I$_2$ | CH$_3$ | |
| 39 | 2-Cl, 3-F | CH$_3$ | |
| 40 | 2-Cl, 4-F | CH$_3$ | |
| 41 | 2-Cl, 5-F | CH$_3$ | |
| 42 | 2-Cl, 6-F | CH$_3$ | |
| 43 | 2-Cl, 3-Br | CH$_3$ | |
| 44 | 2-Cl, 4-Br | CH$_3$ | |
| 45 | 2-Cl, 5-Br | CH$_3$ | |
| 46 | 2-Cl, 6-Br | CH$_3$ | |
| 47 | 2-Br, 3-Cl | CH$_3$ | |
| 48 | 2-Br, 4-Cl | CH$_3$ | |
| 49 | 2-Br, 5-Cl | CH$_3$ | |
| 50 | 2-Br, 3-F | CH$_3$ | |
| 51 | 2-Br, 4-F | CH$_3$ | |
| 52 | 2-Br, 5-F | CH$_3$ | |
| 53 | 2-Br, 6-F | CH$_3$ | |
| 54 | 2-F, 3-Cl | CH$_3$ | |
| 55 | 2-F, 4-Cl | CH$_3$ | |
| 56 | 2-F, 5-Cl | CH$_3$ | |
| 57 | 3-Cl, 4-F | CH$_3$ | |
| 58 | 3-Cl, 5-F | CH$_3$ | |
| 59 | 3-Cl, 4-Br | CH$_3$ | |
| 60 | 3-Cl, 5-Br | CH$_3$ | |
| 61 | 3-F, 4-Cl | CH$_3$ | |
| 62 | 3-F, 4-Br | CH$_3$ | |
| 63 | 3-Br, 4-Cl | CH$_3$ | |
| 64 | 3-Br, 4-F | CH$_3$ | |
| 65 | 2,6-Cl$_2$, 4-Br | CH$_3$ | |
| 66 | 2-CH$_3$ | CH$_3$ | |
| 67 | 3-CH$_3$ | CH$_3$ | 68–72/ 2935,1755, 1603,1213, 1068,1017, 767 |
| 68 | 4-CH$_3$ | CH$_3$ | 80–82/ 2940,1726, 1522,1321, 1215,1068, 1018,805 |
| 69 | 2,3-(CH$_3$)$_2$ | CH$_3$ | |
| 70 | 2,4-(CH$_3$)$_2$ | CH$_3$ | |
| 71 | 2,5-(CH$_3$)$_2$ | CH$_3$ | |
| 72 | 2,6-(CH$_3$)$_2$ | CH$_3$ | |
| 73 | 3,4-(CH$_3$)$_2$ | CH$_3$ | |
| 74 | 3,5-(CH$_3$)$_2$ | CH$_3$ | |
| 75 | 2,3,4-(CH$_3$)$_3$ | CH$_3$ | |
| 76 | 2,3,5-(CH$_3$)$_3$ | CH$_3$ | |
| 77 | 2,3,6-(CH$_3$)$_3$ | CH$_3$ | |
| 78 | 2,4,5-(CH$_3$)$_3$ | CH$_3$ | |
| 79 | 2,4,6-(CH$_3$)$_3$ | CH$_3$ | |
| 80 | 3,4,5-(CH$_3$)$_3$ | CH$_3$ | |
| 81 | 2,3,4,6-(CH$_3$)$_4$ | CH$_3$ | |
| 82 | 2,3,5,6-(CH$_3$)$_4$ | CH$_3$ | |
| 83 | 2,3,4,5,6-(CH$_3$)$_5$ | CH$_3$ | |
| 84 | 2-C$_2$H$_5$ | CH$_3$ | |
| 85 | 3-C$_2$H$_5$ | CH$_3$ | |
| 86 | 4-C$_2$H$_5$ | CH$_3$ | |
| 87 | 2,4-(C$_2$H$_5$)$_2$ | CH$_3$ | |
| 88 | 2,6-(C$_2$H$_5$)$_2$ | CH$_3$ | |
| 89 | 3,5-(C$_2$H$_5$)$_2$ | CH$_3$ | |
| 90 | 2,4,6-(C$_2$H$_5$)$_3$ | CH$_3$ | |
| 91 | 2-n-C$_3$H$_7$ | CH$_3$ | |
| 92 | 3-n-C$_3$H$_7$ | CH$_3$ | |
| 93 | 4-n-C$_3$H$_7$ | CH$_3$ | |
| 94 | 2-i-C$_3$H$_7$ | CH$_3$ | |
| 95 | 3-i-C$_3$H$_7$ | CH$_3$ | |
| 96 | 4-i-C$_3$H$_7$ | CH$_3$ | |
| 97 | 2,4-(i-C$_3$H$_7$)$_2$ | CH$_3$ | |
| 98 | 2,6-(i-C$_3$H$_7$)$_2$ | CH$_3$ | |
| 99 | 3,5-(i-C$_3$H$_7$)$_2$ | CH$_3$ | |
| 100 | 2,4,6-(i-C$_3$H$_7$)$_3$ | CH$_3$ | |
| 101 | 2-s-C$_4$H$_9$ | CH$_3$ | |
| 102 | 3-s-C$_4$H$_9$ | CH$_3$ | |
| 103 | 4-s-C$_4$H$_9$ | CH$_3$ | |
| 104 | 2-t-C$_4$H$_9$ | CH$_3$ | |
| 105 | 3-t-C$_4$H$_9$ | CH$_3$ | |
| 106 | 4-t-C$_4$H$_9$ | CH$_3$ | |
| 107 | 2,3-(t-C$_4$H$_9$)$_2$ | CH$_3$ | |
| 108 | 2,4-(t-C$_4$H$_9$)$_2$ | CH$_3$ | |
| 109 | 2,5-(t-C$_4$H$_9$)$_2$ | CH$_3$ | |
| 110 | 2,6-(t-C$_4$H$_9$)$_2$ | CH$_3$ | |
| 111 | 3,5-(t-C$_4$H$_9$)$_2$ | CH$_3$ | |
| 112 | 2,4,6-(t-C$_4$H$_9$)$_3$ | CH$_3$ | |
| 113 | 4-n-C$_9$H$_{19}$ | CH$_3$ | |
| 114 | 4-n-C$_{12}$H$_{25}$ | CH$_3$ | |
| 115 | 3-n-C$_{15}$H$_{31}$ | CH$_3$ | |
| 116 | 4-(1,1,3,3,-tetramethylbutyl) | CH$_3$ | |
| 117 | 4-(1,1,3,-trimethylbutyl) | CH$_3$ | |
| 118 | 2-t-C$_4$H$_9$, 4-CH$_3$ | CH$_3$ | |
| 119 | 2-t-C$_4$H$_9$, 5-CH$_3$ | CH$_3$ | |
| 120 | 2,6-(t-C$_4$H$_9$)$_2$, 4-CH$_3$ | CH$_3$ | |
| 121 | 2-CH$_3$, 4-t-C$_4$H$_9$ | CH$_3$ | |
| 122 | 2-CH$_3$, 6-t-C$_4$H$_9$ | CH$_3$ | |
| 123 | 2-CH$_3$, 4-i-C$_3$H$_7$ | CH$_3$ | |

TABLE 1-continued (I)

[Structure: Ar-N(X)-CH2-Ar' where the first aryl bears Rm and the second aryl bears a -C(=NOCH3)COOCH3 group]

| No. | $R_m$ | X |
|-----|-------|---|
| 124 | 2-CH₃, 5-i-C₃H₇ | CH₃ |
| 125 | 3-CH₃, 4-i-C₃H₇ | CH₃ |
| 126 | 2-i-C₃H₇, 5-CH₃ | CH₃ |
| 127 | 2,4-(t-C₄H₉)₂, 6-i-C₃H₇ | CH₃ |
| 128 | 2-allyl (C₃H₅) | CH₃ |
| 129 | 3-allyl | CH₃ |
| 130 | 4-allyl | CH₃ |
| 131 | 2-C₃H₅, 6-CH₃ | CH₃ |
| 132 | 2-cyclo-C₆H₁₁ | CH₃ |
| 133 | 3-cyclo-C₆H₁₁ | CH₃ |
| 134 | 4-cyclo-C₆H₁₁ | CH₃ |
| 135 | 2,4-(cyclo-C₆H₁₁)₂, 6-CH₃ | CH₃ |
| 136 | 2-CH₃, 4-cyclo-C₆H₁₁ | CH₃ |
| 137 | 2-CH₃, 4-(1,1,3,3-tetramethylbutyl) | CH₃ |
| 138 | 2-CH₂C₆H₅ | CH₃ |
| 139 | 3-CH₂C₆H₅ | CH₃ |
| 140 | 4-CH₂C₆H₅ | CH₃ |
| 141 | 2-CH₂C₆H₅, 4-CH₃ | CH₃ |
| 142 | 2-CH₃, 4-CH₂C₆H₅ | CH₃ |
| 143 | 2-C₆H₅ | CH₃ |
| 144 | 3-C₆H₅ | CH₃ |
| 145 | 4-C₆H₅ | CH₃ |
| 146 | 4-(2-i-C₃H₇—C₆H₄) | CH₃ |
| 147 | 4-C₆H₅, 2,6-(CH₃)₂ | CH₃ |
| 148 | 2-Cl, 4-C₆H₅ | CH₃ |
| 149 | 2-Br, 4-C₆H₅ | CH₃ |
| 150 | 2-C₆H₅, 4-Cl | CH₃ |
| 151 | 2-C₆H₅, 4-Br | CH₃ |
| 152 | 2-CH₂C₆H₅, 4-Cl | CH₃ |
| 153 | 2-CH₂C₆H₅, 4-Br | CH₃ |
| 154 | 2-Cl, 4-CH₂C₆H₅ | CH₃ |
| 155 | 2-Br, 4-CH₂C₆H₅ | CH₃ |
| 156 | 2-cyclo-C₆H₁₁, 4-Cl | CH₃ |
| 157 | 2-cyclo-C₆H₁₁, 4-Br | CH₃ |
| 158 | 2-Cl, 4-cyclo-C₆H₁₁ | CH₃ |
| 159 | 2-Br, 4-cyclo-C₆H₁₁ | CH₃ |
| 160 | 2-OCH₃ | CH₃ |
| 161 | 3-OCH₃ | CH₃ |
| 162 | 4-OCH₃ | CH₃ |
| 163 | 2,4-(OCH₃)₂ | CH₃ |
| 164 | 2-OC₂H₅ | CH₃ |
| 165 | 3-OC₂H₅ | CH₃ |
| 166 | 4-OC₂H₅ | CH₃ |
| 167 | 2-OCH₂C₆H₅ | CH₃ |
| 168 | 3-OCH₂C₆H₅ | CH₃ |
| 169 | 4-OCH₂C₆H₅ | CH₃ |
| 170 | 2-O-t-C₄H₉ | CH₃ |
| 171 | 3-O-t-C₄H₉ | CH₃ |
| 172 | 4-O-t-C₄H₉ | CH₃ |
| 173 | 2-OC₆H₅ | CH₃ |
| 174 | 3-OC₆H₅ | CH₃ |
| 175 | 4-OC₆H₅ | CH₃ |
| 176 | 2-CF₃ | CH₃ |
| 177 | 3-CF₃ | CH₃ |
| 178 | 4-CF₃ | CH₃ |
| 179 | 2-OCF₃ | CH₃ |
| 180 | 3-OCF₃ | CH₃ |
| 181 | 4-OCF₃ | CH₃ |
| 182 | 3-OCH₂CHF₂ | CH₃ |
| 183 | 3-OCF₂CHF₂ | CH₃ |
| 184 | 3-OC₂F₅ | CH₃ |
| 185 | 2-NO₂ | CH₃ |
| 186 | 3-NO₂ | CH₃ |
| 187 | 4-NO₂ | CH₃ |
| 188 | 2-CN | CH₃ |
| 189 | 3-CN | CH₃ |
| 190 | 4-CN | CH₃ |
| 191 | 2-CH₃, 3-Cl | CH₃ |
| 192 | 2-CH₃, 4-Cl | CH₃ |
| 193 | 2-CH₃, 5-Cl | CH₃ |
| 194 | 2-CH₃, 6-Cl | CH₃ |
| 195 | 2-CH₃, 3-F | CH₃ |
| 196 | 2-CH₃, 4-F | CH₃ |
| 197 | 2-CH₃, 5-F | CH₃ |
| 198 | 2-CH₃, 6-F | CH₃ |
| 199 | 2-CH₃, 3-Br | CH₃ |
| 200 | 2-CH₃, 4-Br | CH₃ |
| 201 | 2-CH₃, 5-Br | CH₃ |
| 202 | 2-CH₃, 6-Br | CH₃ |
| 203 | 2-Cl, 3-CH₃ | CH₃ |
| 204 | 2-Cl, 4-CH₃ | CH₃ |
| 205 | 2-Cl, 5-CH₃ | CH₃ |
| 206 | 2-F, 3-CH₃ | CH₃ |
| 207 | 2-F, 4-CH₃ | CH₃ |
| 208 | 2-F, 5-CH₃ | CH₃ |
| 209 | 2-Br, 3-CH₃ | CH₃ |
| 210 | 2-Br, 4-CH₃ | CH₃ |
| 211 | 2-Br, 5-CH₃ | CH₃ |
| 212 | 3-CH₃, 4-Cl | CH₃ |
| 213 | 3-CH₃, 5-Cl | CH₃ |
| 214 | 3-CH₃, 4-F | CH₃ |
| 215 | 3-CH₃, 5-F | CH₃ |
| 216 | 3-CH₃, 4-Br | CH₃ |
| 217 | 3-CH₃, 5-Br | CH₃ |
| 218 | 3-F, 4-CH₃ | CH₃ |
| 219 | 3-Cl, 4-CH₃ | CH₃ |
| 220 | 3-Br, 4-CH₃ | CH₃ |
| 221 | 2-Cl, 4,5-(CH₃)₂ | CH₃ |
| 222 | 2-Br, 4,5-(CH₃)₂ | CH₃ |
| 223 | 2-Cl, 3,5-(CH₃)₂ | CH₃ |
| 224 | 2-Br, 3,5-(CH₃)₂ | CH₃ |
| 225 | 2,6-Cl₂, 4-CH₃ | CH₃ |
| 226 | 2,6-F₂, 4-CH₃ | CH₃ |
| 227 | 2,6-Br₂, 4-CH₃ | CH₃ |
| 228 | 2,4-Cl₂, 6-CH₃ | CH₃ |
| 229 | 2,4-F₂, 6-CH₃ | CH₃ |
| 230 | 2,4-Br₂, 6-CH₃ | CH₃ |
| 231 | 2,6-(CH₃)₂, 4-F | CH₃ |
| 232 | 2,6-(CH₃)₂, 4-Cl | CH₃ |
| 233 | 2,6-(CH₃)₂, 4-Br | CH₃ |
| 234 | 3,5-(CH₃)₂, 4-F | CH₃ |
| 235 | 3,5-(CH₃)₂, 4-Cl | CH₃ |
| 236 | 3,5-(CH₃)₂, 4-Br | CH₃ |
| 237 | 2,3,6-(CH₃)₃, 4-F | CH₃ |
| 238 | 2,3,6-(CH₃)₃, 4-Cl | CH₃ |
| 239 | 2,3,6-(CH₃)₃, 4-Br | CH₃ |
| 240 | 2,4-(CH₃)₂, 6-F | CH₃ |
| 241 | 2,4-(CH₃)₂, 6-Cl | CH₃ |
| 242 | 2,4-(CH₃)₂, 6-Br | CH₃ |
| 243 | 2-i-C₃H₇, 4-Cl, 5-CH₃ | CH₃ |
| 244 | 2-CH₃, 4-Cl, 5-i-C₃H₇ | CH₃ |
| 245 | 2-Cl, 3-i-C₃H₇ | CH₃ |
| 246 | 2-Cl, 4-i-C₃H₇ | CH₃ |
| 247 | 2-Cl, 4-NO₂ | CH₃ |
| 248 | 2-NO₂, 4-Cl | CH₃ |
| 249 | 2-OCH₃, 5-NO₂ | CH₃ |
| 250 | 2,4-Cl₂, 5-NO₂ | CH₃ |
| 251 | 2,4-Cl₂, 6-NO₂ | CH₃ |
| 252 | 2,6-Cl₂, 4-NO₂ | CH₃ |
| 253 | 2,6-Br₂, 4-NO₂ | CH₃ |
| 254 | 2,6-I₂, 4-NO₂ | CH₃ |
| 255 | H | C₂H₅ |
| 256 | 2-F | C₂H₅ |
| 257 | 3-F | C₂H₅ |
| 258 | 4-F | C₂H₅ |
| 259 | 2,3-F₂ | C₂H₅ |
| 260 | 2,4-F₂ | C₂H₅ |
| 261 | 2,4,6-F₃ | C₂H₅ |
| 262 | 2,3,4,5,6-F₅ | C₂H₅ |
| 263 | 2-Cl | C₂H₅ |
| 264 | 3-Cl | C₂H₅ |

TABLE 1-continued

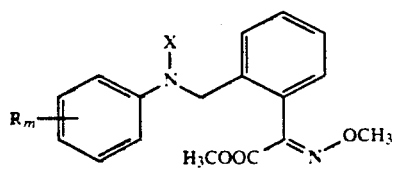

(I)

| No. | $R_m$ | X | mp (°C.)/ IR (cm$^{-1}$) |
|---|---|---|---|
| 265 | 4-Cl | $C_2H_5$ | |
| 266 | 2,3-$Cl_2$ | $C_2H_5$ | |
| 267 | 2,4-$Cl_2$ | $C_2H_5$ | |
| 268 | 2,5-$Cl_2$ | $C_2H_5$ | |
| 269 | 2,6-$Cl_2$ | $C_2H_5$ | |
| 270 | 3,4-$Cl_2$ | $C_2H_5$ | |
| 271 | 3,5-$Cl_2$ | $C_2H_5$ | |
| 272 | 2,3,4-$Cl_3$ | $C_2H_5$ | |
| 273 | 2,3,5-$Cl_3$ | $C_2H_5$ | |
| 274 | 2,3,6-$Cl_3$ | $C_2H_5$ | |
| 275 | 2,4,5-$Cl_3$ | $C_2H_5$ | |
| 276 | 2,4,6-$Cl_3$ | $C_2H_5$ | |
| 277 | 3,4,5-$Cl_3$ | $C_2H_5$ | |
| 278 | 2,3,4,6-$Cl_4$ | $C_2H_5$ | |
| 279 | 2,3,5,6-$Cl_4$ | $C_2H_5$ | |
| 280 | 2,3,4,5,6-$Cl_5$ | $C_2H_5$ | |
| 281 | 2-Br | $C_2H_5$ | |
| 282 | 3-Br | $C_2H_5$ | |
| 283 | 4-Br | $C_2H_5$ | |
| 284 | 2,4-$Br_2$ | $C_2H_5$ | |
| 285 | 2,5-$Br_2$ | $C_2H_5$ | |
| 286 | 2,6-$Br_2$ | $C_2H_5$ | |
| 287 | 2,4,6-$Br_3$ | $C_2H_5$ | |
| 288 | 2,3,4,5,6-$Br_5$ | $C_2H_5$ | |
| 289 | 2-I | $C_2H_5$ | |
| 290 | 3-I | $C_2H_5$ | |
| 291 | 4-I | $C_2H_5$ | |
| 292 | 2,4-$I_2$ | $C_2H_5$ | |
| 293 | 2-Cl, 3-F | $C_2H_5$ | |
| 294 | 2-Cl, 4-F | $C_2H_5$ | |
| 295 | 2-Cl, 5-F | $C_2H_5$ | |
| 296 | 2-Cl, 3-F | $C_2H_5$ | |
| 297 | 2-Cl, 3-Br | $C_2H_5$ | |
| 298 | 2-Cl, 4-Br | $C_2H_5$ | |
| 299 | 2-Cl, 5-Br | $C_2H_5$ | |
| 300 | 2-Cl, 6-Br | $C_2H_5$ | |
| 301 | 2-Br, 3-Cl | $C_2H_5$ | |
| 302 | 2-Br, 4-Cl | $C_2H_5$ | |
| 303 | 2-Br, 5-Cl | $C_2H_5$ | |
| 304 | 2-Br, 3-F | $C_2H_5$ | |
| 305 | 2-Br, 4-F | $C_2H_5$ | |
| 306 | 2-Br, 5-F | $C_2H_5$ | |
| 307 | 2-Br, 6-F | $C_2H_5$ | |
| 308 | 2-F, 3-Cl | $C_2H_5$ | |
| 309 | 2-F, 4-Cl | $C_2H_5$ | |
| 310 | 2-F, 5-Cl | $C_2H_5$ | |
| 311 | 3-Cl, 4-F | $C_2H_5$ | |
| 312 | 3-Cl, 5-F | $C_2H_5$ | |
| 313 | 3-Cl, 4-Br | $C_2H_5$ | |
| 314 | 3-Cl, 5-Br | $C_2H_5$ | |
| 315 | 3-F, 4-Cl | $C_2H_5$ | |
| 316 | 3-F, 4-Br | $C_2H_5$ | |
| 317 | 3-Br, 4-Cl | $C_2H_5$ | |
| 318 | 3-Br, 4-F | $C_2H_5$ | |
| 319 | 2,6-$Cl_2$, 4-Br | $C_2H_5$ | |
| 320 | 2-$CH_3$ | $C_2H_5$ | |
| 321 | 3-$CH_3$ | $C_2H_5$ | |
| 322 | 4-$CH_3$ | $C_2H_5$ | |
| 323 | 2,3-$(CH_3)_2$ | $C_2H_5$ | |
| 324 | 2,4-$(CH_3)_2$ | $C_2H_5$ | |
| 325 | 2,5-$(CH_3)_2$ | $C_2H_5$ | |
| 326 | 2,6-$(CH_3)_2$ | $C_2H_5$ | |
| 327 | 3,4-$(CH_3)_2$ | $C_2H_5$ | |
| 328 | 3,5-$(CH_3)_2$ | $C_2H_5$ | |
| 329 | 2,3,4-$(CH_3)_3$ | $C_2H_5$ | |
| 330 | 2,3,5-$(CH_3)_3$ | $C_2H_5$ | |
| 331 | 2,3,6-$(CH_3)_3$ | $C_2H_5$ | |
| 332 | 2,4,5-$(CH_3)_3$ | $C_2H_5$ | |
| 333 | 2,4,6-$(CH_3)_3$ | $C_2H_5$ | |
| 334 | 3,4,5-$(CH_3)_3$ | $C_2H_5$ | |
| 335 | 2,3,4,6-$(CH_3)_4$ | $C_2H_5$ | |

TABLE 1-continued

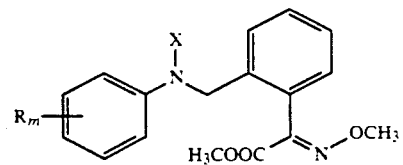

(I)

| No. | $R_m$ | X | mp (°C.)/ IR (cm$^{-1}$) |
|---|---|---|---|
| 336 | 2,3,4,6-$(CH_3)_4$ | $C_2H_5$ | |
| 337 | 2,3,4,5,6-$(CH_3)_5$ | $C_2H_5$ | |
| 338 | 2-$C_2H_5$ | $C_2H_5$ | |
| 339 | 3-$C_2H_5$ | $C_2H_5$ | |
| 340 | 4-$C_2H_5$ | $C_2H_5$ | |
| 341 | 2,4-$(C_2H_5)_2$ | $C_2H_5$ | |
| 342 | 2,6-$(C_2H_5)_2$ | $C_2H_5$ | |
| 343 | 3,5-$(C_2H_5)_2$ | $C_2H_5$ | |
| 344 | 2,4,6-$(C_2H_5)_3$ | $C_2H_5$ | |
| 345 | 2-n-$C_3H_7$ | $C_2H_5$ | |
| 346 | 3-n-$C_3H_7$ | $C_2H_5$ | |
| 347 | 4-n-$C_3H_7$ | $C_2H_5$ | |
| 348 | 2-i-$C_3H_7$ | $C_2H_5$ | |
| 349 | 3-i-$C_3H_7$ | $C_2H_5$ | |
| 350 | 4-i-$C_3H_7$ | $C_2H_5$ | |
| 351 | 2,4-(i-$C_3H_7$)$_2$ | $C_2H_5$ | |
| 352 | 2,6-(i-$C_3H_7$)$_2$ | $C_2H_5$ | |
| 353 | 2,4,6-(i-$C_3H_7$)$_3$ | $C_2H_5$ | |
| 354 | 2,4,6-(i-$C_3H_7$)$_3$ | $C_2H_5$ | |
| 355 | 2-s-$C_4H_9$ | $C_2H_5$ | |
| 356 | 3-s-$C_4H_9$ | $C_2H_5$ | |
| 357 | 4-s-$C_4H_9$ | $C_2H_5$ | |
| 358 | 2-t-$C_4H_9$ | $C_2H_5$ | |
| 359 | 3-t-$C_4H_9$ | $C_2H_5$ | |
| 360 | 4-t-$C_4H_9$ | $C_2H_5$ | |
| 361 | 2,3-(t-$C_4H_9$)$_2$ | $C_2H_5$ | |
| 362 | 2,4-(t-$C_4H_9$)$_2$ | $C_2H_5$ | |
| 363 | 2,5-(t-$C_4H_9$)$_2$ | $C_2H_5$ | |
| 364 | 2,6-(t-$C_4H_9$)$_2$ | $C_2H_5$ | |
| 365 | 3,5-(t-$C_4H_9$)$_2$ | $C_2H_5$ | |
| 366 | 2,4,6-(t-$C_4H_9$)$_3$ | $C_2H_5$ | |
| 367 | 4-n-$C_9H_{19}$ | $C_2H_5$ | |
| 368 | 4-n-$C_{12}H_{25}$ | $C_2H_5$ | |
| 369 | 3-n-$C_{15}H_{31}$ | $C_2H_5$ | |
| 370 | 4-(1,1,3,3-tetramethylbutyl) | $C_2H_5$ | |
| 371 | 4-(1,1,3,-trimethylbutyl) | $C_2H_5$ | |
| 372 | 2-t-$C_4H_9$, 4-$CH_3$ | $C_2H_5$ | |
| 373 | 2-t-$C_4H_9$, 5-$CH_3$ | $C_2H_5$ | |
| 374 | 2,6-(t-$C_4H_9$)$_2$, 4-$CH_3$ | $C_2H_5$ | |
| 375 | 2-$CH_3$, 4-t-$C_4H_9$ | $C_2H_5$ | |
| 376 | 2-$CH_3$, 6-t-$C_4H_9$ | $C_2H_5$ | |
| 377 | 2-$CH_3$, 4-i-$C_3H_7$ | $C_2H_5$ | |
| 378 | 2-$CH_3$, 5-i-$C_3H_7$ | $C_2H_5$ | |
| 379 | 3-$CH_3$, 4-i-$C_3H_7$ | $C_2H_5$ | |
| 380 | 2-i-$C_3H_7$, 5-$CH_3$ | $C_2H_5$ | |
| 381 | 2,4-(t-$C_4H_9$)$_2$, 6-i-$C_3H_7$ | $C_2H_5$ | |
| 382 | 2-allyl ($C_3H_5$) | $C_2H_5$ | |
| 383 | 3-allyl | $C_2H_5$ | |
| 384 | 4-allyl | $C_2H_5$ | |
| 385 | 2-$C_3H_5$, 6-$CH_3$ | $C_2H_5$ | |
| 386 | 2-cyclo-$C_6H_{11}$ | $C_2H_5$ | |
| 387 | 3-cyclo-$C_6H_{11}$ | $C_2H_5$ | |
| 388 | 4-cyclo-$C_6H_{11}$ | $C_2H_5$ | |
| 389 | 2,4-(cyclo-$C_6H_{11}$)$_2$, 6-$CH_3$ | $C_2H_5$ | |
| 390 | 2-$CH_3$, 4-cyclo-$C_6H_{11}$ | $C_2H_5$ | |
| 391 | 2-$CH_3$, 4-(1,1,3,3-tetramethylbutyl) | $C_2H_5$ | |
| 392 | 2-$CH_2C_6H_5$ | $C_2H_5$ | |
| 393 | 3-$CH_2C_6H_5$ | $C_2H_5$ | |
| 394 | 4-$CH_2C_6H_5$ | $C_2H_5$ | |
| 395 | 2-$CH_2C_6H_5$, 4-$CH_3$ | $C_2H_5$ | |
| 396 | 2-$CH_3$, 4-$CH_2C_6H_5$ | $C_2H_5$ | |
| 397 | 2-$C_6H_5$ | $C_2H_5$ | |
| 398 | 3-$C_6H_5$ | $C_2H_5$ | |
| 399 | 4-$C_6H_5$ | $C_2H_5$ | |
| 400 | 4-(2-i-$C_3H_7$—$C_6H_4$) | $C_2H_5$ | |
| 401 | 4-$C_6H_5$, 2,6-$(CH_3)_2$ | $C_2H_5$ | |
| 402 | 2-Cl, 4-$C_6H_5$ | $C_2H_5$ | |
| 403 | 2-Br, 4-$C_6H_5$ | $C_2H_5$ | |
| 404 | 2-$C_6H_5$, 4-Cl | $C_2H_5$ | |
| 405 | 2-$C_6H_5$, 4-Br | $C_2H_5$ | |

TABLE 1-continued (I)

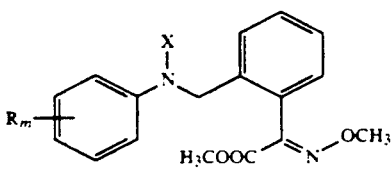

| No. | $R_m$ | X |
|---|---|---|
| 406 | 2-CH$_2$C$_6$H$_5$, 4-Cl | C$_2$H$_5$ |
| 407 | 2-CH$_2$C$_6$H$_5$, 4-Br | C$_2$H$_5$ |
| 408 | 2-Cl, 4-CH$_2$C$_6$H$_5$ | C$_2$H$_5$ |
| 409 | 2-Br, 4-CH$_2$C$_6$H$_5$ | C$_2$H$_5$ |
| 410 | 2-cyclo-C$_6$H$_{11}$, 4-Cl | C$_2$H$_5$ |
| 411 | 2-cyclo-C$_6$H$_{11}$, 4-Br | C$_2$H$_5$ |
| 412 | 2-Cl, 4-cyclo-C$_6$H$_{11}$ | C$_2$H$_5$ |
| 413 | 2-Br, 4-cyclo-C$_6$H$_{11}$ | C$_2$H$_5$ |
| 414 | 2-OCH$_3$ | C$_2$H$_5$ |
| 415 | 3-OCH$_3$ | C$_2$H$_5$ |
| 416 | 4-OCH$_3$ | C$_2$H$_5$ |
| 417 | 2,4-(OCH$_3$)$_2$ | C$_2$H$_5$ |
| 418 | 2-OC$_2$H$_5$ | C$_2$H$_5$ |
| 419 | 3-OC$_2$H$_5$ | C$_2$H$_5$ |
| 420 | 4-OC$_2$H$_5$ | C$_2$H$_5$ |
| 421 | 2-OCH$_2$C$_6$H$_5$ | C$_2$H$_5$ |
| 422 | 3-OCH$_2$C$_6$H$_5$ | C$_2$H$_5$ |
| 423 | 4-OCH$_2$C$_6$H$_5$ | C$_2$H$_5$ |
| 424 | 2-O-t-C$_4$H$_9$ | C$_2$H$_5$ |
| 425 | 3-O-t-C$_4$H$_9$ | C$_2$H$_5$ |
| 426 | 4-O-t-C$_4$H$_9$ | C$_2$H$_5$ |
| 427 | 2-OC$_6$H$_5$ | C$_2$H$_5$ |
| 428 | 3-OC$_6$H$_5$ | C$_2$H$_5$ |
| 429 | 4-OC$_6$H$_5$ | C$_2$H$_5$ |
| 430 | 2-CF$_3$ | C$_2$H$_5$ |
| 431 | 3-CF$_3$ | C$_2$H$_5$ |
| 432 | 4-CF$_3$ | C$_2$H$_5$ |
| 433 | 2-OCF$_3$ | C$_2$H$_5$ |
| 434 | 3-OCF$_3$ | C$_2$H$_5$ |
| 435 | 4-OCF$_3$ | C$_2$H$_5$ |
| 436 | 3-OCH$_2$CHF$_2$ | C$_2$H$_5$ |
| 437 | 3-OCF$_2$CHF$_2$ | C$_2$H$_5$ |
| 438 | 3-OC$_2$F$_5$ | C$_2$H$_5$ |
| 439 | 2-NO$_2$ | C$_2$H$_5$ |
| 440 | 3-NO$_2$ | C$_2$H$_5$ |
| 441 | 4-NO$_2$ | C$_2$H$_5$ |
| 442 | 2-CN | C$_2$H$_5$ |
| 443 | 3-CN | C$_2$H$_5$ |
| 444 | 4-CN | C$_2$H$_5$ |
| 445 | 2-CH$_3$, 3-Cl | C$_2$H$_5$ |
| 446 | 2-CH$_3$, 4-Cl | C$_2$H$_5$ |
| 447 | 2-CH$_3$, 5-Cl | C$_2$H$_5$ |
| 448 | 2-CH$_3$, 6-Cl | C$_2$H$_5$ |
| 449 | 2-CH$_3$, 3-F | C$_2$H$_5$ |
| 450 | 2-CH$_3$, 4-F | C$_2$H$_5$ |
| 451 | 2-CH$_3$, 5-F | C$_2$H$_5$ |
| 452 | 2-CH$_3$, 6-F | C$_2$H$_5$ |
| 453 | 2-CH$_3$, 3-Br | C$_2$H$_5$ |
| 454 | 2-CH$_3$, 4-Br | C$_2$H$_5$ |
| 455 | 2-CH$_3$, 5-Br | C$_2$H$_5$ |
| 456 | 2-CH$_3$, 6-Br | C$_2$H$_5$ |
| 457 | 2-Cl, 3-CH$_3$ | C$_2$H$_5$ |
| 458 | 2-Cl, 4-CH$_3$ | C$_2$H$_5$ |
| 459 | 2-Cl, 5-CH$_3$ | C$_2$H$_5$ |
| 460 | 2-F, 3-CH$_3$ | C$_2$H$_5$ |
| 461 | 2-F, 4-CH$_3$ | C$_2$H$_5$ |
| 462 | 2-F, 5-CH$_3$ | C$_2$H$_5$ |
| 463 | 2-Br, 3-CH$_3$ | C$_2$H$_5$ |
| 464 | 2-Br, 4-CH$_3$ | C$_2$H$_5$ |
| 465 | 2-Br, 5-CH$_3$ | C$_2$H$_5$ |
| 466 | 3-CH$_3$, 4-Cl | C$_2$H$_5$ |
| 467 | 3-CH$_3$, 5-Cl | C$_2$H$_5$ |
| 468 | 3-CH$_3$, 4-F | C$_2$H$_5$ |
| 469 | 3-CH$_3$, 5-F | C$_2$H$_5$ |
| 470 | 3-CH$_3$, 4-Br | C$_2$H$_5$ |
| 471 | 3-CH$_3$, 5-Br | C$_2$H$_5$ |
| 472 | 3-F, 4-CH$_3$ | C$_2$H$_5$ |
| 473 | 3-Cl, 4-CH$_3$ | C$_2$H$_5$ |
| 474 | 3-Br, 4-CH$_3$ | C$_2$H$_5$ |
| 475 | 2-Cl, 4,5-(CH$_3$)$_2$ | C$_2$H$_5$ |
| 476 | 2-Br, 4,5-(CH$_3$)$_2$ | C$_2$H$_5$ |
| 477 | 2-Cl, 3,5-(CH$_3$)$_2$ | C$_2$H$_5$ |
| 478 | 2-Br, 3,5-(CH$_3$)$_2$ | C$_2$H$_5$ |
| 479 | 2,6-Cl$_2$, 4-CH$_3$ | C$_2$H$_5$ |
| 480 | 2,6-F$_2$, 4-CH$_3$ | C$_2$H$_5$ |
| 481 | 2,6-Br$_2$, 4-CH$_3$ | C$_2$H$_5$ |
| 482 | 2,4-Cl$_2$, 6-CH$_3$ | C$_2$H$_5$ |
| 483 | 2,4-F$_2$, 6-CH$_3$ | C$_2$H$_5$ |
| 484 | 2,4-Br$_2$, 6-CH$_3$ | C$_2$H$_5$ |
| 485 | 2,6-(CH$_3$)$_2$, 4-F | C$_2$H$_5$ |
| 486 | 2,6-(CH$_3$)$_2$, 4-Cl | C$_2$H$_5$ |
| 487 | 2,6-(CH$_3$)$_2$, 4-Br | C$_2$H$_5$ |
| 488 | 3,5-(CH$_3$)$_2$, 4-F | C$_2$H$_5$ |
| 489 | 3,5-(CH$_3$)$_2$, 4-Cl | C$_2$H$_5$ |
| 490 | 3,5-(CH$_3$)$_2$, 4-Br | C$_2$H$_5$ |
| 491 | 2,3,6-(CH$_3$)$_3$, 4-F | C$_2$H$_5$ |
| 492 | 2,3,6-(CH$_3$)$_3$, 4-Cl | C$_2$H$_5$ |
| 493 | 2,3,6-(CH$_3$)$_3$, 4-Br | C$_2$H$_5$ |
| 494 | 2,4-(CH$_3$)$_2$, 6-F | C$_2$H$_5$ |
| 495 | 2,4-(CH$_3$)$_2$, 6-Cl | C$_2$H$_5$ |
| 496 | 2,4-(CH$_3$)$_2$, 6-Br | C$_2$H$_5$ |
| 497 | 2-i-C$_3$H$_7$, 4-Cl, 5-CH$_3$ | C$_2$H$_5$ |
| 498 | 2-CH$_3$, 4-Cl, 5-i-C$_3$H$_7$ | C$_2$H$_5$ |
| 499 | 2-Cl, 3-i-C$_3$H$_7$ | C$_2$H$_5$ |
| 500 | 2-Cl, 4-i-C$_3$H$_7$ | C$_2$H$_5$ |
| 501 | 2-Cl, 4-NO$_2$ | C$_2$H$_5$ |
| 502 | 2-NO$_2$, 4-Cl | C$_2$H$_5$ |
| 478 | 2-Br, 3,5-(CH$_3$)$_2$ | C$_2$H$_5$ |
| 479 | 2,6-Cl$_2$, 4-CH$_3$ | C$_2$H$_5$ |
| 480 | 2,6-F$_2$, 4-CH$_3$ | C$_2$H$_5$ |
| 481 | 2,6-Br$_2$, 4-CH$_3$ | C$_2$H$_5$ |
| 482 | 2,4-Cl$_2$, 6-CH$_3$ | C$_2$H$_5$ |
| 483 | 2,4-F$_2$, 6-CH$_3$ | C$_2$H$_5$ |
| 484 | 2,4-Br$_2$, 6-CH$_3$ | C$_2$H$_5$ |
| 485 | 2,6-(CH$_3$)$_2$, 4-F | C$_2$H$_5$ |
| 486 | 2,6-(CH$_3$)$_2$, 4-Cl | C$_2$H$_5$ |
| 487 | 2,6-(CH$_3$)$_2$, 4-Br | C$_2$H$_5$ |
| 488 | 3,5-(CH$_3$)$_2$, 4-F | C$_2$H$_5$ |
| 489 | 3,5-(CH$_3$)$_2$, 4-Cl | C$_2$H$_5$ |
| 490 | 3,5-(CH$_3$)$_2$, 4-Br | C$_2$H$_5$ |
| 491 | 2,3,6-(CH$_3$)$_3$, 4-F | C$_2$H$_5$ |
| 492 | 2,3,6-(CH$_3$)$_3$, 4-Cl | C$_2$H$_5$ |
| 493 | 2,3,6-(CH$_3$)$_3$, 4-Br | C$_2$H$_5$ |
| 494 | 2,4-(CH$_3$)$_2$, 6-F | C$_2$H$_5$ |
| 495 | 2,4-(CH$_3$)$_2$, 6-Cl | C$_2$H$_5$ |
| 496 | 2,4-(CH$_3$)$_2$, 6-Br | C$_2$H$_5$ |
| 497 | 2-i-C$_3$H$_7$, 4-Cl, 5-CH$_3$ | C$_2$H$_5$ |
| 498 | 2-CH$_3$, 4-Cl, 5-i-C$_3$H$_7$ | C$_2$H$_5$ |
| 499 | 2-Cl, 3-i-C$_3$H$_7$ | C$_2$H$_5$ |
| 500 | 2-Cl, 4-i-C$_3$H$_7$ | C$_2$H$_5$ |
| 501 | 2-Cl, 4-NO$_2$ | C$_2$H$_5$ |
| 502 | 2-NO$_2$, 4-Cl | C$_2$H$_5$ |
| 503 | 2-OCH$_3$, 5-NO$_2$ | C$_2$H$_5$ |
| 504 | 2,4-Cl$_2$, 5-NO$_2$ | C$_2$H$_5$ |
| 505 | 2,4-Cl$_2$, 6-NO$_2$ | C$_2$H$_5$ |
| 506 | 2,6-Cl$_2$, 4-NO$_2$ | C$_2$H$_5$ |
| 507 | 2,6-Br$_2$, 4-NO$_2$ | C$_2$H$_5$ |
| 508 | 2,6-I$_2$, 4-NO$_2$ | C$_2$H$_5$ |
| 509 | H | H |
| 510 | 2-F | H |
| 511 | 3-F | H |
| 512 | 4-F | H |
| 513 | 2,3-F$_2$ | H |
| 514 | 2,4-F$_2$ | H |
| 515 | 2,4,6-F$_3$ | H |
| 516 | 2,3,4,5,6-F$_5$ | H |
| 517 | 2-Cl | H |
| 518 | 3-Cl | H |
| 519 | 4-Cl | H |
| 520 | 2,3-Cl$_2$ | H |
| 521 | 2,4-Cl$_2$ | H |
| 522 | 2,5-Cl$_2$ | H |

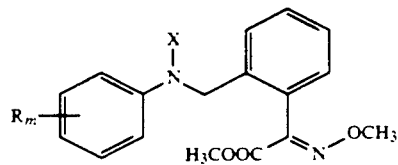

TABLE 1-continued

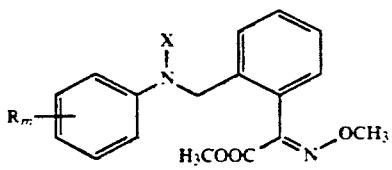

(I)

| No. | $R_m$ | X | mp (°C.)/ IR (cm$^{-1}$) |
|---|---|---|---|
| 523 | 2,6-Cl$_2$ | H | |
| 524 | 3,4-Cl$_2$ | H | |
| 525 | 3,5-Cl$_2$ | H | |
| 526 | 2,3,4-Cl$_3$ | H | |
| 527 | 2,3,5-Cl$_3$ | H | |
| 528 | 2,3,6-Cl$_3$ | H | |
| 529 | 2,4,5-Cl$_3$ | H | |
| 530 | 2,4,6-Cl$_3$ | H | |
| 531 | 3,4,5-Cl$_3$ | H | |
| 532 | 2,3,4,6-Cl$_4$ | H | |
| 533 | 2,3,5,6-Cl$_4$ | H | |
| 534 | 2,3,4,5,6-Cl$_5$ | H | |
| 535 | 2-Br | H | |
| 536 | 3-Br | H | |
| 537 | 4-Br | H | |
| 538 | 2,4-Br$_2$ | H | |
| 539 | 2,5-Br$_2$ | H | |
| 540 | 2,6-Br$_2$ | H | |
| 541 | 2,4,6-Br$_3$ | H | |
| 542 | 2,3,4,5,6-Br$_5$ | H | |
| 543 | 2-I | H | |
| 544 | 3-I | H | |
| 545 | 4-I | H | |
| 546 | 2,4-I$_2$ | H | |
| 547 | 2-Cl, 3-F | H | |
| 548 | 2-Cl, 4-F | H | |
| 549 | 2-Cl, 5-F | H | |
| 550 | 2-Cl, 6-F | H | |
| 551 | 2-Cl, 3-Br | H | |
| 552 | 2-Cl, 4-Br | H | |
| 553 | 2-Cl, 5-Br | H | |
| 554 | 2-Cl, 6-Br | H | |
| 555 | 2-Br, 3-Cl | H | |
| 556 | 2-Br, 4-Cl | H | |
| 357 | 2-Br, 5-Cl | H | |
| 558 | 2-Br, 3-F | H | |
| 559 | 2-Br, 4-F | H | |
| 560 | 2-Br, 5-F | H | |
| 561 | 2-Br, 6-F | H | |
| 562 | 2-F, 3-Cl | H | |
| 563 | 2-F, 4-Cl | H | |
| 564 | 2-F, 5-Cl | H | |
| 565 | 3-Cl, 4-F | H | |
| 566 | 3-Cl, 5-F | H | |
| 567 | 3-Cl, 4-Br | H | |
| 568 | 3-Cl, 5-Br | H | |
| 569 | 3-F, 4-Cl | H | |
| 570 | 3-F, 4-Br | H | |
| 571 | 3-Br, 4-Cl | H | |
| 572 | 3-Br, 4-F | H | |
| 573 | 2,6-Cl$_2$, 4-Br | H | |
| 574 | 2-CH$_3$ | H | |
| 575 | 3-CH$_3$ | H | |
| 576 | 4-CH$_3$ | H | |
| 577 | 2,3-(CH$_3$)$_2$ | H | |
| 578 | 2,4-(CH$_3$)$_2$ | H | |
| 579 | 2,5-(CH$_3$)$_2$ | H | |
| 580 | 2,6-(CH$_3$)$_2$ | H | |
| 581 | 3,4-(CH$_3$)$_2$ | H | |
| 582 | 3,5-(CH$_3$)$_2$ | H | |
| 583 | 2,3,4-(CH$_3$)$_3$ | H | |
| 584 | 2,3,5-(CH$_3$)$_3$ | H | |
| 585 | 2,3,6-(CH$_3$)$_3$ | H | |
| 586 | 2,4,5-(CH$_3$)$_3$ | H | |
| 587 | 2,4,6-(CH$_3$)$_3$ | H | |
| 588 | 3,4,5-(CH$_3$)$_3$ | H | |
| 589 | 2,3,4,6-(CH$_3$)$_4$ | H | |
| 590 | 2,3,5,6-(CH$_3$)$_4$ | H | |
| 591 | 2,3,4,5,6-(CH$_3$)$_5$ | H | |
| 592 | 2-C$_2$H$_5$ | H | |
| 593 | 3-C$_2$H$_5$ | H | |

TABLE 1-continued

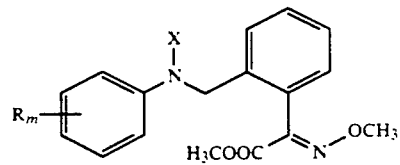

(I)

| No. | $R_m$ | X | mp (°C.)/ IR (cm$^{-1}$) |
|---|---|---|---|
| 594 | 4-C$_2$H$_5$ | H | |
| 595 | 2,4-(C$_2$H$_5$)$_2$ | H | |
| 596 | 2,6-(C$_2$H$_5$)$_2$ | H | |
| 597 | 3,5-(C$_2$H$_5$)$_2$ | H | |
| 598 | 2,4,6-(C$_2$H$_5$)$_3$ | H | |
| 599 | 2-n-C$_3$H$_7$ | H | |
| 600 | 3-n-C$_3$H$_7$ | H | |
| 601 | 4-n-C$_3$H$_7$ | H | |
| 602 | 2-i-C$_3$H$_7$ | H | |
| 603 | 3-i-C$_3$H$_7$ | H | |
| 604 | 4-i-C$_3$H$_7$ | H | |
| 605 | 2,4-(i-C$_3$H$_7$)$_2$ | H | |
| 606 | 2,6-(i-C$_3$H$_7$)$_2$ | H | |
| 607 | 2,4,6-(i-C$_3$H$_7$)$_3$ | H | |
| 608 | 2,4,6-(i-C$_3$H$_7$)$_3$ | H | |
| 609 | 2-s-C$_4$H$_9$ | H | |
| 610 | 3-s-C$_4$H$_9$ | H | |
| 611 | 4-s-C$_4$H$_9$ | H | |
| 612 | 2-t-C$_4$H$_9$ | H | |
| 613 | 3-t-C$_4$H$_9$ | H | |
| 614 | 4-t-C$_4$H$_9$ | H | |
| 615 | 2,3-(t-C$_4$H$_9$)$_2$ | H | |
| 616 | 2,4-(t-C$_4$H$_9$)$_2$ | H | |
| 617 | 2,5-(t-C$_4$H$_9$)$_2$ | H | |
| 618 | 2,6-(t-C$_4$H$_9$)$_2$ | H | |
| 619 | 3,5-(t-C$_4$H$_9$)$_2$ | H | |
| 620 | 2,4,6-(t-C$_4$H$_9$)$_3$ | H | |
| 621 | 4-n-C$_9$H$_{19}$ | H | |
| 622 | 4-n-C$_{12}$H$_{25}$ | H | |
| 623 | 3-n-C$_{15}$H$_{31}$ | H | |
| 624 | 4-(1,1,3,3,-tetramethylbutyl) | H | |
| 625 | 4-(1,1,3,-trimethylbutyl) | H | |
| 626 | 2-t-C$_4$H$_9$, 4-CH$_3$ | H | |
| 627 | 2-t-C$_4$H$_9$, 5-CH$_3$ | H | |
| 628 | 2,6-(t-C$_4$H$_9$)$_2$, 4-CH$_3$ | H | |
| 629 | 2-CH$_3$, 4-t-C$_4$H$_9$ | H | |
| 630 | 2-CH$_3$, 6-t-C$_4$H$_9$ | H | |
| 631 | 2-CH$_3$, 4-i-C$_3$H$_7$ | H | |
| 632 | 2-CH$_3$, 5-i-C$_3$H$_7$ | H | |
| 633 | 3-CH$_3$, 4-i-C$_3$H$_7$ | H | |
| 634 | 2-i-C$_3$H$_7$, 5-CH$_3$ | H | |
| 635 | 2,4-(t-C$_4$H$_9$)$_2$, 6-i-C$_3$H$_7$ | H | |
| 636 | 2-allyl (C$_3$H$_5$) | H | |
| 637 | 3-allyl | H | |
| 638 | 4-allyl | H | |
| 639 | 2-C$_3$H$_5$, 6-CH$_3$ | H | |
| 640 | 2-cyclo-C$_6$H$_{11}$ | H | |
| 641 | 3-cyclo-C$_6$H$_{11}$ | H | |
| 642 | 4-cyclo-C$_6$H$_{11}$ | H | |
| 643 | 2,4-(cyclo-C$_6$H$_{11}$)$_2$, 6-CH$_3$ | H | |
| 644 | 2-CH$_3$, 4-cyclo-C$_6$H$_{11}$ | H | |
| 645 | 2-CH$_3$, 4-(1,1,3,3-tetramethylbutyl) | H | |
| 646 | 2-CH$_2$C$_6$H$_5$ | H | |
| 647 | 3-CH$_2$C$_6$H$_5$ | H | |
| 648 | 4-CH$_2$C$_6$H$_5$ | H | |
| 649 | 2-CH$_2$C$_6$H$_5$, 4-CH$_3$ | H | |
| 650 | 2-CH$_3$, 4-CH$_2$C$_6$H$_5$ | H | |
| 651 | 2-C$_6$H$_5$ | H | |
| 652 | 3-C$_6$H$_5$ | H | |
| 653 | 4-C$_6$H$_5$ | H | |
| 654 | 4-(2-i-C$_3$H$_7$—C$_6$H$_4$) | H | |
| 655 | 4-C$_6$H$_5$, 2,6-(CH$_3$)$_2$ | H | |
| 656 | 2-Cl, 4-C$_6$H$_5$ | H | |
| 657 | 2-Br, 4-C$_6$H$_5$ | H | |
| 658 | 2-C$_6$H$_5$, 4-Cl | H | |
| 659 | 2-C$_6$H$_5$, 4-Br | H | |
| 660 | 2-CH$_2$C$_6$H$_5$, 4-Cl | H | |
| 661 | 2-CH$_2$C$_6$H$_5$, 4-Br | H | |
| 662 | 2-Cl, 4-CH$_2$C$_6$H$_5$ | H | |
| 663 | 2-Br, 4-CH$_2$C$_6$H$_5$ | H | |

TABLE 1-continued

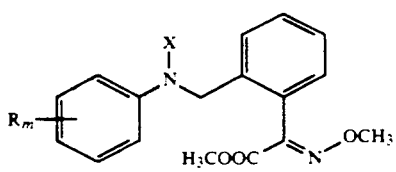

(I)

| No. | $R_m$ | X |
|---|---|---|
| 664 | 2-cyclo-$C_6H_{11}$, 4-Cl | H |
| 665 | 2-cyclo-$C_6H_{11}$, 4-Br | H |
| 666 | 2-Cl, 4-cyclo-$C_6H_{11}$ | H |
| 667 | 2-Br, 4-cyclo-$C_6H_{11}$ | H |
| 668 | 2-$OCH_3$ | H |
| 669 | 3-$OCH_3$ | H |
| 670 | 4-$OCH_3$ | H |
| 671 | 2,4-$(OCH_3)_2$ | H |
| 672 | 2-$OC_2H_5$ | H |
| 673 | 3-$OC_2H_5$ | H |
| 674 | 4-$OC_2H_5$ | H |
| 675 | 2-$OCH_2C_6H_5$ | H |
| 676 | 3-$OCH_2C_6H_5$ | H |
| 677 | 4-$OCH_2C_6H_5$ | H |
| 678 | 2-O-t-$C_4H_9$ | H |
| 679 | 3-O-t-$C_4H_9$ | H |
| 680 | 4-O-t-$C_4H_9$ | H |
| 681 | 2-$OC_6H_5$ | H |
| 682 | 3-$OC_6H_5$ | H |
| 683 | 4-$OC_6H_5$ | H |
| 684 | 2-$CF_3$ | H |
| 685 | 3-$CF_3$ | H |
| 686 | 4-$CF_3$ | H |
| 687 | 2-$OCF_3$ | H |
| 688 | 3-$OCF_3$ | H |
| 689 | 4-$OCF_3$ | H |
| 690 | 3-$OCH_2CHF_2$ | H |
| 691 | 3-$OCF_2CHF_2$ | H |
| 692 | 3-$OC_2F_5$ | H |
| 693 | 2-$NO_2$ | H |
| 694 | 3-$NO_2$ | H |
| 695 | 4-$NO_2$ | H |
| 696 | 2-CN | H |
| 697 | 3-CN | H |
| 698 | 4-CN | H |
| 699 | 2-$CH_3$, 3-Cl | H |
| 700 | 2-$CH_3$, 4-Cl | H |
| 701 | 2-$CH_3$, 5-Cl | H |
| 702 | 2-$CH_3$, 6-Cl | H |
| 703 | 2-$CH_3$, 3-F | H |
| 704 | 2-$CH_3$, 4-F | H |
| 705 | 2-$CH_3$, 5-F | H |
| 706 | 2-$CH_3$, 6-F | H |
| 707 | 2-$CH_3$, 3-Br | H |
| 708 | 2-$CH_3$, 4-Br | H |
| 709 | 2-$CH_3$, 5-Br | H |
| 710 | 2-$CH_3$, 6-Br | H |
| 711 | 2-Cl, 3-$CH_3$ | H |
| 712 | 2-Cl, 4-$CH_3$ | H |
| 713 | 2-Cl, 5-$CH_3$ | H |
| 714 | 2-F, 3-$CH_3$ | H |
| 715 | 2-F, 4-$CH_3$ | H |
| 716 | 2-F, 5-$CH_3$ | H |
| 717 | 2-Br, 3-$CH_3$ | H |
| 718 | 2-Br, 4-$CH_3$ | H |
| 719 | 2-Br, 5-$CH_3$ | H |
| 720 | 3-$CH_3$, 4-Cl | H |
| 721 | 3-$CH_3$, 5-Cl | H |
| 722 | 3-$CH_3$, 4-F | H |
| 723 | 3-$CH_3$, 5-F | H |
| 724 | 3-$CH_3$, 4-Br | H |
| 725 | 3-$CH_3$, 5-Br | H |
| 726 | 3-F, 4-$CH_3$ | H |
| 727 | 3-Cl, 4-$CH_3$ | H |
| 728 | 3-Br, 4-$CH_3$ | H |
| 729 | 2-Cl, 4,5-$(CH_3)_2$ | H |
| 730 | 2-Br, 4,5-$(CH_3)_2$ | H |
| 731 | 2-Cl, 3,5-$(CH_3)_2$ | H |
| 732 | 2-Br, 3,5-$(CH_3)_2$ | H |
| 733 | 2,6-$Cl_2$, 4-$CH_3$ | H |
| 734 | 2,6-$F_2$, 4-$CH_3$ | H |
| 735 | 2,6-$Br_2$, 4-$CH_3$ | H |
| 736 | 2,4-$Cl_2$, 6-$CH_3$ | H |
| 737 | 2,4-$F_2$, 6-$CH_3$ | H |
| 738 | 2,4-$Br_2$, 6-$CH_3$ | H |
| 739 | 2,6-$(CH_3)_2$, 4-F | H |
| 740 | 2,6-$(CH_3)_2$, 4-Cl | H |
| 741 | 2,6-$(CH_3)_2$, 4-Br | H |
| 742 | 3,5-$(CH_3)_2$, 4-F | H |
| 743 | 3,5-$(CH_3)_2$, 4-Cl | H |
| 744 | 3,5-$(CH_3)_2$, 4-Br | H |
| 745 | 2,3,6-$(CH_3)_3$, 4-F | H |
| 746 | 2,3,6-$(CH_3)_3$, 4-Cl | H |
| 747 | 2,3,6-$(CH_3)_3$, 4-Br | H |
| 748 | 2,4-$(CH_3)_2$, 6-F | H |
| 749 | 2,4-$(CH_3)_2$, 6-Cl | H |
| 750 | 2,4-$(CH_3)_2$, 6-Br | H |
| 751 | 2-i-$C_3H_7$, 4-Cl, 5-$CH_3$ | H |
| 752 | 2-$CH_3$, 4-Cl, 5-i-$C_3H_7$ | H |
| 753 | 2-Cl, 3-i-$C_3H_7$ | H |
| 754 | 2-Cl, 4-i-$C_3H_7$ | H |
| 755 | 2-Cl, 4-$NO_2$ | H |
| 756 | 2-$NO_2$, 4-Cl | H |
| 757 | 2-$OCH_3$, 5-$NO_2$ | H |
| 758 | 2,4-$Cl_2$, 5-$NO_2$ | H |
| 759 | 2,4-$Cl_2$, 6-$NO_2$ | H |
| 760 | 2,6-$Cl_2$, 4-$NO_2$ | H |
| 761 | 2,6-$Br_2$, 4-$NO_2$ | H |
| 762 | 2,6-$I_2$, 4-$NO_2$ | H |
| 763 | 2-$CH_3$ | n-$C_3H_7$ |
| 764 | 2-$CH_3$ | i-$C_3H_7$ |
| 765 | 2-$CH_3$ | cyclo-$C_3H_5$ |
| 766 | 2-$CH_3$ | cyclo-$C_3H_5$ |
| 767 | 2-$CH_3$ | cyclo-$C_5H_9$ |
| 768 | 2-$CH_3$ | cyclo-$C_6H_{11}$ |
| 769 | 2-$CH_3$ | n-$C_4H_9$ |
| 770 | 2-$CH_3$ | i-$C_4H_9$ |
| 771 | 2-$CH_3$ | s-$C_4H_9$ |
| 772 | 2-$CH_3$ | t-$C_4H_9$ |
| 773 | 2-$CH_3$ | n-$C_5H_{11}$ |
| 774 | 2-$CH_3$ | n-$C_6H_{13}$ |
| 775 | H | n-$C_3H_7$ |
| 776 | H | i-$C_3H_7$ |
| 777 | H | cyclo-$C_3H_5$ |
| 778 | H | cyclo-$C_3H_5$ |
| 779 | H | cyclo-$C_5H_9$ |
| 780 | H | cyclo-$C_6H_{11}$ |
| 781 | H | n-$C_4H_9$ |
| 782 | H | n-$C_5H_{11}$ |
| 783 | H | n-$C_6H_{13}$ |
| 784 | *1) | $CH_3$ |
| 785 | *1) | $C_2H_5$ |
| 786 | *1) | H |
| 787 | *2) | $CH_3$ |
| 788 | *2) | $C_2H_5$ |
| 789 | *2) | H |

*1)
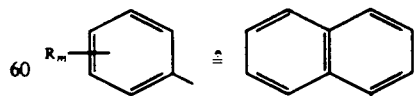

*2)
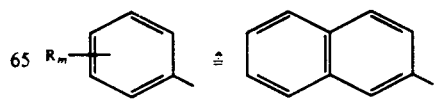

The aniline derivatives I are extremely effective on a broad spectrum of phytopathogenic fungi, in particular those from the class consisting of the Ascomycetes and Basidiomycetes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:

*Erysiphe graminis* in cereals,
*Erysiphe cichoracearum* and *Sphaerotheca fuliginea* in cucurbits,
*Podosphaera leucotricha* in apples,
*Uncinula necator* in vines,
Puccinia species in cereals,
*Rhizoctonia solani* in cotton,
Ustilago species in cereals and sugar cane,
*Venturia inaequalis* (scab) in apples,
Helminthosporium species in cereals,
*Septoria nodorum* in wheat,
*Botrytis cinerea* (gray mold) in strawberries and grapes,
*Cercospora arachidicola* in groundnuts,
*Pseudocercosporella herpotrichoides* in wheat and barley,
*Pyricularia oryzae* in rice,
*Phytophthora infestans* in potatoes and tomatoes,
Fusarium and Verticillium species in various plants,
*Plasmopara viticola* in grapes,
Alternaria species in fruit and vegetables.

The compounds are applied by spraying or dusting the plants with the active ingredients, or treating the seeds of the plants with the active ingredients. They may be applied before or after infection of the plants or seeds by the fungi. It is possible to treat either the fungi themselves, or the plants, seeds, materials or the soil to be protected against fungus attack.

The compounds can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin, sulfite waste liquors and methylcellulose.

The fungicides generally contain from 0.1 to 95, and preferably from 0.5 to 90, wt % of active ingredient. The application rates are from 0.02 to 3 kg or more of active ingredient per hectare, depending on the type of effect desired. The compounds I may also be used for protecting materials (timber) e.g., against *Paecilomyces variotii*. When the active ingredients are used for treating seed, amounts of from 0.001 to 50, and preferably from 0.01 to 10, g per kg of seed are generally sufficient.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. A solution of 90 parts by weight of compound no. 1 and 10 parts by weight of N-methyl-α-pyrrolidone, which is suitable for application in the form of very fine drops.

II. A mixture of 20 parts by weight of compound no. 1, 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By finely dispersing the mixture in water, an aqueous dispersion is obtained.

III. An aqueous dispersion of 20 parts by weight of compound no. 4, 40 parts by weight of cyclohexanone, 30 parts by weight of isobutanol, and 20 parts by weight of the adduct of 40 moles of ethylene oxide and 1 mole of castor oil. An aqueous dispersion is obtained by pouring the solution into water and finely distributing it therein.

IV. An aqueous dispersion of 20 parts by weight of compound no. 68, 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. An aqueous dispersion is obtained by pouring the solution into water and finely distributing it therein.

V. A hammer-milled mixture of 80 parts by weight of compound no. 4, 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel. By finely dispersing the mixture in water, a spray liquor is obtained.

VI. An intimate mixture of 3 parts by weight of compound no. 68 and 97 parts by weight of particulate kaolin. The dust contains 3 wt % of the active ingredient.

VII. An intimate mixture of 30 parts by weight of compound no. 1, 92 parts by weight of powdered silica gel and 8 parts by weight of paraffin oil sprayed onto the surface of this silica gel. This formulation of the active ingredient exhibits good adherence.

VIII. A stable aqueous dispersion of 40 parts by weight of compound no. 4, 10 parts of the sodium salt of a phenosulfonic acid-urea-formaldehyde condensate, 2 parts of silica gel and 48 parts of water, which dispersion can be further diluted.

IX. A stable oily dispersion of 20 parts by weight of compound no. 1, 2 parts by weight of the calcium salt of dodecylbenzenesulfonic acid, 8 parts by weight of a fatty polyglycol ether, 2 parts by weight of the sodium salt of a phenosulfonic acid-urea-formaldehyde condensate and 68 parts by weight of a paraffinic mineral oil.

In these application forms, the fungicidal agents according to the invention may also be present together with other active ingredients, for example herbicides, insecticides, growth regulators, and fungicides, and may furthermore be mixed and applied together with fertilizers. Admixture with other fungicides often results in a greater fungicidal action spectrum.

USE EXAMPLE

EXAMPLE 1

5-Action on *Pyrenophora teres*

Barley seedlings of the "Igri" variety were sprayed to runoff at the 2-leaf stage with aqueous suspensions containing (dry basis) 80% of active ingredient and 20% emulsifier. After 24 hours the plants were inoculated with a spore suspension of the fungus *Pyrenophora teres* and placed for 48 hours in a high-humidity climatic cabinet kept at 18° C. The plants were then cultivated for a further 5 days in the greenhouse at 20°-22° C. and a relative humidity of 70%. The extent of fungus spread was then determined.

The compound 2-phenoxymethylphenylglyoxylic acid methyl ester-O-methyloxime disclosed in DE-A-3,623,921 (compound no. 124) was used for comparison purposes.

The results show that for instance compound no. 1 according to the invention has a fungicidal action far superior to that of the prior art active ingredient.

We claim:

1. Aniline derivatives of the formula I

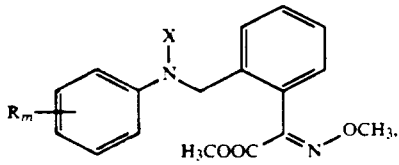

(I)

where
R is hydrogen, halogen, cyano, nitro, $C_1-C_{15}$-alkyl, $C_3-C_6$-cycloalkyl, $C_3-C_6$-alkenyl, $C_1-C_4$-alkoxy, $C_1-C_2$-haloalkyl, $C_1-C_2$-haloalkoxy, substituted or unsubstituted phenyl, substituted or unsubstituted phenoxy, benzyl, halobenzyl having up to three halo substituents, or substituted or unsubstituted benzyloxy, wherein the substituents of substituted phenyl, substituted phenoxy, and substituted benzyloxy are up to 3 substituents independently selected from the group consisting of halo and $C_1-C_4$-alkyl, m is an integer of from 1 to 5 or the group

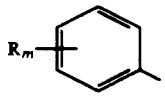

is α-naphthyl or β-naphthyl and
X is hydrogen, $C_1-C_6$-alkyl or $C_3-C_6$-cycloalkyl, or a plant-tolerated acid addition salt or metal complex thereof.

2. An aniline derivative of the formula I as set forth in claim 1, where $R_m$ is hydrogen and X is methyl.

3. An aniline derivative of the formula I as set forth in claim 1, where $R_m$ is 4-fluorine and X is methyl.

4. An aniline derivative of the formula I as set forth in claim 1, where $R_m$ is 4-methyl and X is methyl.

5. A fungicidal composition containing an inert carrier and a fungicidally effective amount of an aniline derivative of the formula I

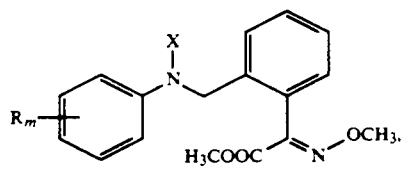

(I)

where
R is hydrogen, halogen, cyano, nitro, $C_1-C_{15}$-alkyl, $C_3-C_6$-cycloalkyl, $C_3-C_6$-alkenyl, $C_1-C_4$-alkoxy, $C_1-C_2$-haloalkyl, $C_1-C_2$-haloalkoxy, substituted or unsubstituted phenyl, substituted or unsubstituted phenoxy, benzyl, halobenzyl having up to three halo substituents, or substituted or unsubstituted benzyloxy, wherein the substituents of substituted phenyl, substituted phenoxy, and substituted benzyloxy are up to 3 substituents independently selected from the group consisting of halo and $C_1-C_4$-alkyl, m is an integer of from 1 to 5 or the group

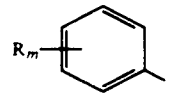

is α-naphthyl or β-naphthyl and
X is hydrogen, $C_1-C_6$-alkyl or $C_3-C_6$-cycloalkyl, or a plant-tolerated acid addition salt or metal complex thereof.

6. A process for combating fungi, wherein the fungi or the materials, plants, seed or the soil to be protected against fungus attack are treated with a fungicidally effective amount of an aniline derivative of the formula I

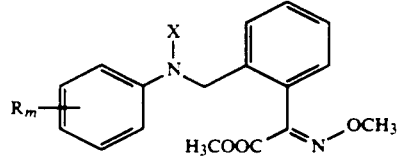

where
R is hydrogen, halogen, cyano, nitron, $C_1-C_{15}$-alkyl, $C_3-C_6$-cycloalkyl, $C_3-C_6$-alkenyl, $C_1-C_4$-alkoxy, $C_1-C_2$-haloalkyl, $C_1-C_2$-haloalkoxy, substituted or unsubstituted phenyl, substituted or unsubstituted phenoxy, benzyl, halobenzyl having up to three halo substituents, or substituted or unsubstituted benzyloxy, wherein the substituents of substituted phenyl, substituted phenoxy, and substituted benzyloxy are up to 3 substituents independently selected from the group consisting of halo and $C_1-C_4$-alkyl, m is an integer of from 1 to 5 or the group

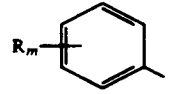

is α-naphthyl or β-naphthyl and
X is hydrogen, $C_1-C_6$-alkyl or $C_3-C_6$-cycloalkyl, or a plant-tolerated acid addition salt or metal complex thereof.

* * * * *